United States Patent
Zeldis

(10) Patent No.: US 7,863,297 B2
(45) Date of Patent: *Jan. 4, 2011

(54) METHODS OF USING 4-(AMINO)-2-(2,6-DIOXO(3-PIPERIDLY))-ISOINDOLINE-3-DIONE FOR THE TREATMENT OF MYELODYSPLASTIC SYNDROMES

(75) Inventor: Jerome B. Zeldis, Princeton, NJ (US)

(73) Assignee: Celgene Corporation, Summit, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/985,032

(22) Filed: Nov. 12, 2007

(65) Prior Publication Data

US 2008/0161360 A1    Jul. 3, 2008

Related U.S. Application Data

(60) Continuation of application No. 11/654,550, filed on Jan. 16, 2007, now Pat. No. 7,393,863, which is a division of application No. 10/411,649, filed on Apr. 11, 2003, now Pat. No. 7,189,740.

(60) Provisional application No. 60/418,468, filed on Oct. 15, 2002.

(51) Int. Cl.
A61K 31/445 (2006.01)

(52) U.S. Cl. .................................................. 514/323

(58) Field of Classification Search ............. 424/131.1; 514/58, 319, 323
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,810,643 A | 3/1989 | Souza | |
| 4,999,291 A | 3/1991 | Souza | |
| 5,059,595 A | 10/1991 | LeGrazie | |
| 5,073,543 A | 12/1991 | Marshall et al. | |
| 5,120,548 A | 6/1992 | McClelland et al. | |
| 5,134,127 A | 7/1992 | Stella et al. | |
| 5,229,496 A | 7/1993 | Deeley et al. | |
| 5,288,487 A | 2/1994 | Kawashima et al. | |
| 5,354,556 A | 10/1994 | Sparks et al. | |
| 5,385,901 A | 1/1995 | Kaplan et al. | |
| 5,391,485 A | 2/1995 | Deeley et al. | |
| 5,393,870 A | 2/1995 | Deeley et al. | |
| 5,528,823 A | 6/1996 | Rudy et al. | |
| 5,580,755 A | 12/1996 | Souza | |
| 5,591,767 A | 1/1997 | Mohr et al. | |
| 5,593,990 A | 1/1997 | D'Amato | |
| 5,629,327 A | 5/1997 | D'Amato | |
| 5,635,517 A | 6/1997 | Muller et al. | |
| 5,639,476 A | 6/1997 | Oshlack et al. | |
| 5,643,915 A | 7/1997 | Andrulis et al. | |
| 5,674,533 A | 10/1997 | Santus et al. | |
| 5,698,579 A | 12/1997 | Muller | |
| 5,712,291 A | 1/1998 | D'Amato | |
| 5,733,566 A | 3/1998 | Lewis | |
| 5,798,368 A | 8/1998 | Muller et al. | |
| 5,874,448 A | 2/1999 | Muller et al. | |
| 5,877,200 A | 3/1999 | Muller | |
| 5,929,117 A | 7/1999 | Muller et al. | |
| 5,955,476 A | 9/1999 | Muller et al. | |
| 6,011,050 A | 1/2000 | Muller et al. | |
| 6,071,948 A | 6/2000 | D'Amato | |
| 6,096,757 A | 8/2000 | Bishop et al. | |
| 6,228,879 B1 | 5/2001 | Green et al. | |
| 6,281,230 B1 | 8/2001 | Muller et al. | |
| 6,316,471 B1 * | 11/2001 | Muller et al. | 514/323 |
| 6,335,349 B1 | 1/2002 | Muller et al. | |
| 6,380,239 B1 | 4/2002 | Muller et al. | |
| 6,395,754 B1 | 5/2002 | Muller et al. | |
| 6,403,613 B1 | 6/2002 | Man et al. | |
| 6,420,414 B1 | 7/2002 | D'Amato | |
| 6,458,810 B1 | 10/2002 | Muller et al. | |
| 6,469,045 B1 | 10/2002 | D'Amato | |

(Continued)

FOREIGN PATENT DOCUMENTS

JP    11-286455    10/1999

(Continued)

OTHER PUBLICATIONS

Strasser et al, Thalimdomide treatment in multiple myeloma, Science Direct-Blood review, Sep. 20, 2002.*

(Continued)

*Primary Examiner*—Michael G Hartley
*Assistant Examiner*—Jagadishwar R Samala
(74) *Attorney, Agent, or Firm*—Jones Day

(57) ABSTRACT

Methods of treating, preventing and/or managing myelodysplastic syndromes are disclosed. Specific methods encompass the administration of an immunomodulatory compound, or a pharmaceutically acceptable salt, solvate, hydrate, stereoisomer, clathrate, or prodrug thereof, alone or in combination with a second active ingredient, and/or the transplantation of blood or cells. Specific second active ingredients are capable of affecting or blood cell production. Pharmaceutical compositions, single unit dosage forms, and kits suitable for use in methods of the invention are also disclosed.

17 Claims, No Drawings

U.S. PATENT DOCUMENTS

| | | | |
|---|---|---|---|
| 6,476,052 | B1 | 11/2002 | Muller et al. |
| 6,518,298 | B2 | 2/2003 | Green et al. |
| 6,673,828 | B1 | 1/2004 | Green et al. |
| 7,189,740 | B2 * | 3/2007 | Zeldis .................. 514/323 |
| 7,393,863 | B2 * | 7/2008 | Zeldis .................. 514/323 |
| 2001/0021380 | A1 | 9/2001 | Pluenneke |
| 2001/0056114 | A1 | 12/2001 | D'Amato |
| 2002/0035090 | A1 | 3/2002 | Zeldis et al. |
| 2002/0045643 | A1 | 4/2002 | Muller et al. |
| 2002/0052398 | A1 | 5/2002 | D'Amato |
| 2002/0054899 | A1 | 5/2002 | Zeldis |
| 2002/0061923 | A1 | 5/2002 | D'Amato |
| 2002/0161023 | A1 | 10/2002 | D'Amato |
| 2002/0173658 | A1 | 11/2002 | Muller et al. |
| 2002/0183360 | A1 | 12/2002 | Muller et al. |
| 2003/0028028 | A1 | 2/2003 | Man et al. |
| 2003/0045552 | A1 | 3/2003 | Robarge et al. |
| 2003/0069428 | A1 | 4/2003 | Muller et al. |
| 2003/0096841 | A1 | 5/2003 | Robarge et al. |
| 2003/0139451 | A1 | 7/2003 | Shah et al. |
| 2003/0144325 | A1 | 7/2003 | Muller et al. |
| 2003/0181428 | A1 | 9/2003 | Green et al. |
| 2003/0187024 | A1 | 10/2003 | D'Amato |
| 2003/0191098 | A1 | 10/2003 | D'Amato |
| 2003/0235909 | A1 | 12/2003 | Hariri et al. |
| 2004/0029832 | A1 | 2/2004 | Zeldis |
| 2004/0077685 | A1 | 4/2004 | Figg et al. |
| 2004/0077686 | A1 | 4/2004 | Dannenberg et al. |
| 2004/0087546 | A1 | 5/2004 | Zeldis |
| 2004/0091455 | A1 | 5/2004 | Zeldis |
| 2004/0122052 | A1 | 6/2004 | Muller et al. |

FOREIGN PATENT DOCUMENTS

| | | | |
|---|---|---|---|
| WO | WO 92/06712 | | 4/1992 |
| WO | WO 98/03502 | | 1/1998 |
| WO | WO 98/54170 | | 12/1998 |
| WO | WO 01/87306 | | 11/2001 |
| WO | WO 01/87307 | | 11/2001 |
| WO | WO 01/87307 | A2 * | 11/2001 |
| WO | WO 02/059106 | | 8/2002 |
| WO | PCT/US03/11323 | | 9/2003 |
| WO | WO 03/097040 | | 11/2003 |
| WO | WO 03/097052 | | 11/2003 |
| WO | WO 2004/035064 | | 4/2004 |
| WO | WO 2005/110085 | | 11/2005 |
| WO | WO 2005/110408 | | 11/2005 |

OTHER PUBLICATIONS

Raza et al., Thalidomide produces transfusion independence in . . . Blood, Aug. 15, 2001, vol. 98(4), pp. 958-965.*
Muller et al., Amino-substituted thalidomide analogs: Potent inhinbitors . . . Bioorganic & Medicinal Chemistry Letter, vol. 9, 1625-1630, 1999.*
Marriott et al., Immunotherapeutic and antitumor potential of thalidomide analogues, Epert Opin. Biol. Ther, 1(4), 675-682, 2001.*
U.S. Appl. No. 60/372,348, filed Apr. 12, 2002, Hariri et al.
Beazley et al., 1985, "Malignant stricture at the confluence of the biliary tree: diagnosis and management," *Surg. Annu.* 17:125-41.
Bennett et al., 1985, "Proposed revised criteria for the classification of acute myeloid leukemia. A report of the French-American-British Cooperative Group," *Ann. Intern. Med.* 103(4):620-625.
Besa, 1992, "Myelodysplastic syndromes (refractory anemia). A perspective of the biologic, clinical, and therapeutic issues," *Med. Clin. North Am.* 76(3):599-617.
Besa et al., 1990, 76(Supp. 1):133a.
Bowen et al., 1991, "The treatment of anaemia in the myelodysplastic syndromes with recombinant human erythropoietin," *Br. J. Haematol.* 77(3):419-423.
Cartensen, 1995, *Drug Stability: Principles & Practice*, 2nd ed., Marcel Dekker, New York, NY pp. 379-380.
Corral et al., 1999, *Ann. Rheum. Dis.* 58(Supp. 1):1107-1113.
Costa et al., 1998, *Blood* 92(10:suppl. 1):235b, Abstract #4007.
D'Amato et al., 1994, "Thalidoide is an inhibitor of angiogenesis," *PNAS USA* 91(9):4082-4085.
Dexter, 1989, "Haemopoietic growth factors," *Br. Med. Bull.* 45(2):337-349.
Dexter, 1998, "Growth factors involved in haemopoiesis." *J. Cell. Sci.* 88 ( Pt 1):1-6.
Dredge et al., 2002, "Novel thalidomide analogues display anti-angiogenic activity independently of immunomodulatory effects," *Br. J. Cancer* 87(10):1166-1172.
Ehrenpreis et al., 1999 "Thalidomide therapy for patients with refractory Crohn's disease: an open-label trial," *Gastroenterology* 117(6):1271-1277.
Emens et al., 2001 "Chemotherapy: friend or foe to cancer vaccines?" *Curr. Opin. Mol. Ther.* 3(1):77-84.
Golde et al., 1988 "Hormones that stimulate the growth of blood cells," *Sci. Am.* 259(1):62-71.
Goldberg et al., 1990, "Survey of exposure to genotoxic agents in primary myelodysplastic syndrome: correlation with chromosome patterns and data on patients without hematological disease," *Cancer Res.* 50(21):6876-6881.
Greenberg et al., 1997, "International scoring system for evaluating prognosis in myelodysplastic syndromes," *Blood* 89(6):2079-2088.
Gupta et al., 2001, "Adherences of multiple myeloma cells to bone marrow stromal cells upregulates vascular endothelial growth factor secretion: therapeutic applications," *Leukemia* 15:1950-1961.
Handman et al., 1979, "Stimulation by granulocyte-macrophage colony-stimulating factor of Leishmania tropica killing by macrophage," *J. Immunol.* 122(3):1134-1137.
Harris et al., 1999, "World Health Organization classification of neoplastic diseases of the hematopoietic and lymphoid tissues: report of the Clinical Advisory Committee meeting-Airlie House, Virginia, Nov. 1997," *J. Clin. Oncol.* 17(12):3855-3849.
Hellstrom et al., 1990, 76(Supp. 1):279a.
Koch, 1985, "Thalidomide and congeners as anti-inflammatory agents," *Prog. Med. Chem.* 22:165-242.
Kropff, 2000, *Blood* 96(11 part 1):168a.
Kurland et al., 1979, "Induction of prostaglandin E synthesis in normal and neoplastic macrophages: role for colony-stimulating factor(s) distinct from effects on myeloid progenitor cell proliferation," *Proc. Natl. Acad. Sci. USA* 76(5):2326-2330.
Lentzsch et al., 2003, "Immunomodulatory analogs of thalidomide inhibit growth of Hs Sultan cells and angiogenesis in vivo," *Leukimia*17(1):41-44.
List, 2002, ASH Abstract #521.
Marriott et al., 2001, "Immunotherapeutic and antitumour potential of thalidomide analogues," *Expert Opin. Biol. Ther.* 1(4):675-682.
McCann, 1999, *Drug Topics* pp. 41-42 (Jun. 21, 1999).
*The Merck Manual*, 1999, 17$^{th}$ ed., pp. 953-955.
Metcalf, 1985, "The granulocyte-macrophage colony-stimulating factors," *Science* 229(4708):16-22.
Moller et al., 1997, "Inhibition of IL-12 production by thalidomide," *J. Immunol.* 159(10):5157-5161.
Moore, 1991, "The clinical use of colony stimulating factors," *Ann. Rev. Immunol.* 9:159-191.
Moore et al., 1980, "Production of lymphocyte-activating factor (Interleukin 1) by macrophages activated with colony-stimulating factors," *J. Immunol.* 125(3):1302-1305.
Muller et al., 1999, "Amino-substituted thalidomide analogs: potent inhibitors of TNF-alpha production," *Bioorg. Med. Chem. Lett.* 9(11):1625-1630.
Muller et al., 1998, "Thalidomide analogs and PDE4 inhibition," *Bioorg. Med. Chem. Lett.* 8(19):2669-2674.
Muller et al., 1996, "Structural modifications of thalidomide produce analogs with enhanced tumor necrosis factor inhibitory activity," *J. Med. Chem.* 39(17):3238-3240.
Munshi et al., 1999, *Blood* 94(10 part 1):578a.
Ogawa, 1989, "Hemopoietic stem cells: stochastic differentiation and humoral control of proliferation," *Environ. Health Perspect.* 80:199-207.
Payvandi et al., 2003, ASCO Abstract #992.

Penichet et al., 2001, "Antibody-cytokine fusion proteins for the therapy of cancer," *J. Immunol. Methods.* 248(1-2):91-101.

*Physicians' Desk Reference*, 2002, 56the ed. pp. 582-592, 1154-1158, 1755-1760.

Raza et al., 2001, "Thalidomide Produces Transfusion Independence in Long-standing Refractory Anemias of Patients with Myelodysplastic Syndromes," *Blood* 98(4):958-965.

Schrader et al., 1981, "The persisting (P) cell: histamine content, regulation by a T cell-derivied factor, origin from a bone marrow precursor and relationship to mast cells," *Proc. Natl. Acad. Sci. USA* 78(1):323-327.

Schuster et al., 1990, *Blood* 76(Supp. 1):318a.

Singhal et al. 1999, "Antitumor activity of thalidomide in refractory multiple myeloma," *N. Engl. J. Med.* 341(21):1565-1571.

Stanley et al., 1976, "Factors regulating macrophage production and growth: identity of colony-stimulating factor and macrophage growth factor," *J. Exp. Med.* 143(3):631-647.

Tabbara et al., 1991, "Hematopietic growth factors," *Anticancer Res.* 11(1):81-90.

Vadas et al., 1983, "Eosinophil activation by colony-stimulating factor in man: matabolic effects and analysis by flow cytometry," *Blood* 61(6):1232-1241.

Vadas et al., 1983, "Activation of antibody-dependent cell-mediated cytotoxicity of human neutrophils and eosinophils by seperate colony-stimulating factors," *J. Immunol.* 130(2):795-799.

Vasiliauskas et al., 1999, "An open-label pilot study of low-dose thalidomide in chronically active, steroid-dependent Crohn's disease," *Gastroenterology* 117(6):1278-1287.

Weisbart et al., 1986, "Biosynthetic human GM-CSF modulates the number and affinity of neutrophil f-Met-Leu-Phe receptors," *J. Immunol.* 137(11):3584-3587.

Wolff, ed., 1995, *Burger's Medicinal Chemistry and Drug Discovery*, 5$^{th}$ ed., pp. 172-178, 949-982.

Goerner et al., 2002, Morbidity and mortality of chronic GVHD after hematopoietic stem cell transplantation from HLA-identical siblings for patients with aplastic or refractory anemias, *Biology of Blood and Marrow Transplantation* (Abstract only) 8(1):47-56, accessed from Database STN/CAPLUS, Fred Hutchinson Cancer Research Center and the University of Washington, Seattle, WA, Accession No. 2002:1195127.

Kurzrock, 2002, "Myelodysplastic syndrome overview," *Seminars in Hematology* (Abstract only) (Suppl. 2) 39(3).

N. Ake Jonnson, 1972, "Chemical Structure and Teratogenic Properties," ACTA Pharm., pp. 521-542.

Bellamy et al., 2001, "Vascular endothelial cell growth factor is an autocrine promoter of abnormal localized immature myeloid precursor and leukemia progenitor formation in myelodysplastic syndromes," *Blood* 97:1427-1434.

Bennett et al.,1982, "Proposals for the classification of the myelodysplastic syndromes," *Br. J. Haematol.* 51:189-199.

Bumm et al., 2003, "Emergences of clonal cytogenic abnormalities in pH- cells in some CML patients in cytogenic remission to imatinib but restoration of polyclonal hematopoiesis in the majority," *Blood* 101:1941-1949.

Cancer Therapy Evaluation Program, 1998, "Common toxicity criteria," Version 2.0, Bethesda, MD: Division of Cancer Treatment and Diagnosis, National Institutes of Health, Mar. 1998. (Accessed Jan. 18, 2005, at http://ctep.cancer.gov/reporting/ctc.html.).

Cheson et al., 2000, "Report of an international working group to standardize response criteria for myelodysplastic syndromes," *Blood* 96:3671-3674.

Claessens et al., 2002, "In vitro proliferation and differentiation of erythroid progenitors from patients with myelodysplastic syndromes: evidence for Fas-dependent apoptosis," *Blood* 99:1594-1601.

Corral et al., 1999, "Differential cytokine modulation and T cell activation by two distinct classes of thalidomide analogues that are potent inhibitors of TNF-alpha," *J. Immunol.* 163:380-386.

Davies et al., 2001, "Thalidomide and immunomodulatory derivatives augment natural killer cell cytotoxicity in multiple myeloma," *Blood* 98:210-216.

Deeg et al., 2002, "Soluble TNF receptor fusion protein (etanercept) for the treatment of myelodysplastic syndrome: a pilot study," *Leukemia* 16:162-164.

Gersuk et al., 1996, "Fas (CD95) receptor and Fas-ligand expression in bone marrow cells from patients with myelodysplastic syndrome," *Blood* 88(3):1122-1123.

Goldberg et al., 2003, "Myelodysplastic subclones in chronic myeloid leukemia: implications for imatinib mesylate therapy," *Blood* 101:781.

He, W., et al., 1993, Abstract of papers, 206th American Chemical Society, Chicago, IL; Med. Chem., paper 216.

Hellstrom-Lindberg et al., 1997, "Erythroid response to treatment with G-CSF plus erythropoietin for the anaemia of patients with myelodysplastic syndromes: proposal for a predictive model," *Br. J. Haematol.* 99:344-351.

Jaffe et al., eds., 2001, "World Health Organization classification of tumours: pathology and genetics of tumours of haematopoietic and lymphoid tissues," Lyon, France: IARC Press pp. 61-74.

Kaplan et al., 1958, "Nonparametric estimation from incomplete observations," J. Am. Stat. Assoc. 53:457-481.

Kitagawa et al., 1997, "Overexpression of tumor necrosis factor (TNF)-α and interferon (INF)-γ by bone marrow cells from patients with myelodysplastic syndromes," *Leukemia* 11:2049-2054.

List et al., 2005, "Efficacy of Lenalidomide in myelodysplastic syndromes," N. Engl. J. Med. 352(6):549-557.

List et al., 2004, "Myelodysplastic syndromes," Wintrobe's Clinical Hematology, 11$^{th}$ ed., Philadelphia: Lippincott Williams & Wilkins pp. 2207-2234.

List et al., 2004, "Vascular endothelial growth factor receptor-1 and receptor-2 initiate a phosphatidylinositide 3-kinase-dependent clonogenic response in acute myeloid leukemia cells," Exp. Hematol. 32:526-535.

Maciejewski et al., 2002, "A pilot study of the recombinant soluble human tumour necrosis factor receptor (p75)-Fc fusion protein in patients with myelodysplastic syndrome," Br. J. Haematol. 117:119.

Moreira et al., 1993, "Thalidomide exerts its inhibitory action on tumor necrosis factor alpha by enhancing mRNA degradation," J. Exp. Med. 177:1675-1680.

Peddie et al., 1997, "Oxidative DNA damage in CD34+ myelodysplastic cells in associated with intracellular redox changes and elevated plasma tumor necrosis factor-α concentration," Br. J. Haematol. 99:625-631.

Rajapaksa et al., 1996, Altered oncoprotein expression and apoptosis in myelodysplastic syndrome marrow cells,: Blood 88:4275-4287.

Raza et al., 1995, "Apoptosis in bone marrow biopsy samples involving stromal and hematopoietic cells in 50 patients with myelodysplastic syndromes," Blood 86:268-276.

Richardson et al., 2002, "Immunmodulatory drug CC-5013 overcomes drug resistance and is well tolerated in patients with relapsed multiple myeloma," Blood 100:3063-3067.

Rose et al., 1995, "The use of r-HuEpo in the treatment of anaemia related to myelodysplasia (MDS)," Br. J. Haematol. 89:831-837.

Tauro et al., 2002, "Functional disturbance of marrow stromal microenvironment in the myelodysplastic syndromes," Leukemia 16:785-790.

Turk et al., 1996, "Binding of thalidomide to alpha1-acid glycoprotein may be involved in its inhibition of tumor necrosis factor alpha production," PNAS USA 93:7552-7556.

Hideshima et al., 2000, "Thalidomide and its analogs overcome drug resistance of human multiple myeloma cells to conventional therapy," Blood 96(9):2943-2950.

Baker, AF; Bellamy, WT; Glinsmann-Gibson, B; Heaton, R.; Buresh, A.; Grogan, TM; List, AF; "Biological response to Thalidomide in Remitting Patients with Myelodysplastic Syndrome (MDS) Evidence for Induction of Neoplastic Vascular Endothelial Growth Factor (VEGF) Resistance" Blood 2001:98(11):353a-4a, Abstract #1490.

Bours, V; Franzoso, G; Brown, K.; Park, S.; Azarenko, V.; Tomita-Yamaguchi, M.; Kelly, K.; Siebenilist, U.; "Lymphocyte Activation and the Family of NF-kB Transcription Facor Complexes." Corrent Topics in Microbiology and Immunology, 1992, 182: 411-20.

List, AF; Pharmacological Differentiation and Anti-Apoptic Therapy in Myelodysplastic Syndromes; "Forum Trends in Experimental and Clinical Medicine," 9:35-45,1999.

List, AF; Brasfield, F.; Heaton, R.; Glinsmann-Gibson, B.; Crook, L.; Taetle, R.; Capizzi, R.; Stimulation of Hematopoiesis by Amifostine in Paitents with Myelodysplattic Syndrom. Blood 1997, 90(9): 3364-9.

List, AF; "New Approaches to the Treatment of Myelodysplastia," The ONcologist 2002, 7 Suppl. 1:39-49.

Thomas, D.A., Aguayo, A., Estey, E., Albitar, M., O'Brien, S., Giles, F.J., Beran, M., Cortes, J., Zeldis, J., Keating, M.J., Barlogie, B., Kantarjian, H.M., Thalidomide as anti-angiogenesis therapy (rx) in refractory or relapsed leukemia. Abstract #2269, American Society of Hematology, Dec. 3-7, 1999.

Raza, A., Lisak, L., Andrews, C., Little, L., Muzammil, M., Alvi, S., Mazzoran, L., Zorat, F., Akber, A., Ekbal, M., Razvi, S., Venugopal, P., Thalidomide produces transfusion independence in patients with long-standing refractory anemias and myelodysplastic syndromes (MDS). Abstract #2935, Amer. Soc. of Hematology, Dec. 3-7, 1999.

Raza, A., Lisak, L., Andrews, C., Little, L., Zorat, F., Shetty, V., Alvi, S., Mundle, S., Allampallam, K., Durandt, M., Ekbal, M., Muzammil, M., Encouraging improvement in cytopenias of patients with myelodysplastic syndromes (MDS) with thalidomide. Abstract #111, Amer. Soc. of Clinical Oncology, May 20-23, 2000.

Raza, A., Lisak, L., Little, L., Dean, L., Gezer, S., Venugopal, V., Summary and future direction of anti-tumor necrosis factor (TNF) therapies in myelodysplastic syndromes (MDS). Abstract #2700, American Society of Hematology, May 12-17, 2001.

Mundle, S., Zorat, F., Shetty, V., Allampallam, K., Alvi, S., Lisak, L., Little, L., Dean, L., Nascimben, F., Ekbal, M., Durandt, M., Broderick, E., Venugopal, P., Raza, A., Thalidomide in myelodysplasia. Abstract #626, American Society of Hematology, Dec. 1-5, 2000.

Raza, A., Lisak, L., Little, L., Ekbal, M., Durandt, M., Ali, E., Nascimben, F., Tareen, M., Venugopal, P., Thalidomide as a single agent or in combination with topotecan, pentoxifylline and/or enbrel in myelodysplastic syndromes (MDS). Abstract #627, American Society of Hematology, Dec. 1-5, 2000.

Estey, E., Albitar, M., Cortes, J., Giles, F., Thomas, D., Koller, C., Beran, M., Kantarjian, H., Addition of thalidomide(T) to chemotherapy did not increase remission rate in poor prognosis AML/MDS. Abstract #1394, American Society of Hematology, Dec. 1-5, 2000.

Alvi, S., Henderson, B., Shaher, A., Dangerfield, B., Broderick, E., Jafri, N., Tareen, M., Durandt, M., Galili, N., Borok, R.Z., Raza, A., Determination of clonality in stromal and parenchymal cells pre and post thalidomide treatment in myelodysplasia. Abstract #1536, American Society of Hematology, Dec. 1-5, 2000.

Alvi, S., Shaher, A., Henderson, B., Dar, S., Zorat, F., Broderick E., Lisak, L., Durandt, M., Reddy, P., Mundle, S., Galili, N, Borok, R.Z., Raza, A., Improved growth of stromal cells in long term bone marrow cultures (LTBMC) of myelodysplastic syndrome (MDS) patients treated with thalidomide. Abstract #1547, American Society of Hematology, Dec. 1-5, 2000.

Dourado, C. Mc., Seixas-Silva Jr., J.A., Besa, E.C., Response to thalidomide in 9 patients with myelodysplastic syndromes: A promising treatment for early or post-chemotherapy in late forms of MDS. Abstract #4855, American Society of Hematology, Dec. 1-5, 2000.

Lisak, L.A., Little, L., Dean, L., Ekbal, M., Durandt, M., Hussain, M., Kaistha, V., Raza, A., Delayed responses to thalidomide in patients with myelodysplastic syndromes. Abstract #4861, American Society of Hematology, Dec. 1-5, 2000.

Anders, O., Plath, F., Emmrich, J., Freund, M., Complete remission of therapy-resistant angiodysplasia of the stomach in myelodysplastic syndrome following thalidomide. Abstract #3820, American Society of Hematology, Dec. 7-11, 2001.

Alvi, S., Shaher, A., Shaikh, M., Anthwal, S., Siddiqi, F., Akhtar, A., Ashraf, H., Meager, R., Mundle, S., Shetty, V., Goldberg, C., Galili, N., Borok, R.Z., Raza, A., MDS patients with hematological response to thalidomide show enhanced in vitro growth potential. Abstract #1482, American Society of Hematology, Dec. 7-11, 2001.

Alvi, S., Shaikh, M., Anthwal, S., Shaher, A., Tamoseviciene, D., Novick, A., Reddy, P., Allampallam, K., Hsu, W.T., Galili, N., Borok, R.Z., Raza, A., Cytogenetic and clonal profile of myelodysplastic syndromes (MDS) patients treated with thalidomide. Abstract #1483, American Society of Hematology, Dec. 7-11, 2001.

Alvi, S., Anthwal, S., Shaikh, M., Shaher, A., Shetty, V., Mundle, S., Reddy P., Allampallam, K., Bi, S., Zorat, F., Tamosveiciene, D., Rasila, K., Meagher, R., Westbrook, C., Galili, N., Gezer, S., Venugopal, P., Borok, R.Z., Raza, A., Thalidomide significantly augments proliferation and cytokine secretion to bone marrow cultures established from myelodysplastic syndrome (MDS) patients. Abstract #1484, American Society of Hematology, Dec. 7-11, 2001.

Baker, A.F., Bellamy, W.T., Glinsmann-Gibson, B.J., Heaton, R., Buresh, A., Grogan, T.M., List, A.F., Biological response to thalidomide in remitting patients with myelodysplastic syndrome (MDS): Evidence for induction of neoplastic muscular endothelial growth factor (VEGF) resistance. Abstract #1490, American Society of Hematology, Dec. 7-11, 2001.

Musto, P., Falcone, A., Bodenizza, C., Sanpaolo, G., Matera, R., Bisceglia, M., Carella, A.M., Thalidomide (THAL) significantly improves anemia in selected transfusion-dependent patients with myelodysplastic syndromes (MDS): relationship to serum and marrow levels of angiogenetic growth factors (AGF). Abstract #2606, American Society of Hematology. Dec. 7-11, 2001.

Fabbri, A., Biscardi, M., Innocenti, F., Balestri, G., Gavazzi, S., Bellesi, G., Grossi, A., Thalidomide in combination with Amifostine in the treatment of MDS: evaluation of clinical and laboratory findings. Abstract #4819, American Society of Hematology, Dec. 7-11, 2001.

Raza, A., Lisak, L., Dutt, D., Dean, L., Fantroy, L., Ali, E., Gezer, S., Hsu, W-T., Goldberg, C., Loew, J., Venugopal, P., Combination of thalidomide with pentoxifylline, ciprofloxacin, and dexamethasone (PCD) in patients with myelodysplastic syndromes (MDS). Abstract #4830, American Society of Hematology, Dec. 7-11, 2001.

Raza, A., Dutt, D., Lisak, L., Dean, L., Fantroy, L., Gezer, S., Ali, E., Goldberg, C., Loew, J., Hsu, W-T., Venugopal, P., Combination of thalidomide and enbrel for the treatment of patients with myelodysplastic syndromes (MDS). Abstract #4831. American Society of Hematology. Dec. 7-11, 2001.

Shetty, V., Allampallam, K., Hussaini, S., Townsend, W., Dutt, D., Mundle, S., Alvi, S., Reddy, P.L., Ashraf, H., Galili, N., Saberwal, G.S., Anthwal, S., Shaikh, M.W., Heidelberg, A., Lisak, L., Gezer, S., Venugopal, P., Raza, A., Effects of anti-cytokine agents on apoptosis, proliferation, monocyte/macrophage number, microvessel density and cytokines following two successive clinical trials in 57 patients with myelodysplastic syndromes (MDS). Abstract #4837. American Society of Hematology, Dec. 7-11, 2001.

Barlogie, B., Desikan, R., Munshi, N., Siegel, D., Mehta, J., Singhal, S., Anaissie, E., Single Course D.T. Pace Anti-Angiochemotherapy Effects CR in Plasma Cell Leukemia and Fulminant Multiple Myeloma (MM). Abstract #4180. American Society of Hematology, Dec. 4-9, 1998.

Hideshima, T., Chauhan, D., Shima, Y., Noopur, R., Davies, F.E., Tai, Y., Treon, S.P., Lin, B.K., Schlossman, R.L., Richardson, P.G., Gupta, D., Muller, G.W., Stirling, D.I., Anderson, K.C., Thalidome (THAL) and its Analogs Overcome Drug Resistance of Human Multiple Myeloma (MM) Cells to Conventional Therapy. Abstract #1313. American Society of Hematology, Dec. 1-5, 2000.

Payvandi, F., Wu, L., Gupta, D., Hideshima, T., Haley, M., Muller, G., Chen, R., Anderson, K.C., Stirling, D., Effects of a Thalidomide Analog on Binding Activity of Transcription Factors and Cell Cycle Progression of Multiple Myeloma Cell Lines. Abstract #2487. American Society of Hematology, Dec. 1-5, 2000.

Davies, F.E., Raje, N., Hideshima, T., Lentzsch, S., Young, G., Tai, Y., Lin, B.K., Podar, K., Chauhan, D., Treon, S.P., Gupta, D., Mitsiades, C., Mitsiades, N., Hayashi, T., Richardson, P.G., Schlossman, R.L., Muller, G.W., Stirling, D. I., Anderson, K.C., Thalidomide (THAL) and Immunomodulatory Derivatives (IMiDS) Augment Natural Killer (NK) Cell Cytotocixity in Multiple Myeloma (MM). Abstract #3617. American Society of Hematology, Dec. 1-5, 2000.

Hideshima, T., Chauhan, D., Castro, A., Hayashi, T., Mitsiades, C., Mitsiades, N., Akiyama, M., Richardson, P.G., Schlossman, R.L., Adams, J., Anderson, K.C., NF-KB as a Therapeutic Target in Multiple Myeloma (MM). Abstract #1581. American Society of Hematology, Dec. 7-11, 2001.

Lentsch, S., Rogers, M., Leblanc, R., Birsner, A., Shah, J., Anderson K., D'Amato R., 3-Amino-Phthalimido-Glutarimide (S-3APG) Inhibits Angiogenesis and Growth in Drug Resistant Multiple Myeloma (MM) in vivo. Abstract #1976, American Society of Hematology, Dec. 7-11, 2001.

Park, Y., Kim, S.A., Kim, C.J., Chung, J.H., Mechanism of the Effect of Thalidomide on Human Multiple Myeloma Cells. Abstract #2685. American Society of Clinical Oncology, May 12-17, 2001.

Payvandi, F., Wu, L., Haley M., Gupta, D., Zhang, L., Schafer, P., Muller, G.W., Chen, R., Anderson, K.C., Stirling, D., Thalidomide Analogs IMiDS Inhibit Expression of Cyclooxygenase-2 in Multiple Myeloma Cell Line and LPS Stimulated PBMCs. Abstract #2689. American Society of Hematology, Dec. 7-11, 2001.

Mitsiades, N., Mitsiades, C., Poulaki, V., Akiyama, M., Tai, Y., Lin, B., Hayashi T., Catley, L, Hideshima, T., Chauhan, D., Treon, S.P., Anderson, K.C., Apoptotic Signaling Induced by Immunomodulatory Thalidomide Analogs (Imids) in Human Multiple Myeloma Cells; Therapeutic Implications. Abstract #3224. American Society of Hematology, Dec. 7-11, 2001.

Richardson, P.G., Schlossman, R.L., Hideshima, T., Davies, F., Leblanc, R., Catley, L., Doss, D., Kelly, K.A., Mckenney, M., Mechlowicz, J., Freeman, A,. Deocampo, R., Rich, R., Ryoo, J., Chauhan, D., Munshi, N., Weller, E., Zeldis, J., Anderson, K.C., A Phase 1 Study of Oral CC5013, an Immunomodulatory Thalidomide (Thal) Derivative, in Patients With Relapsed and Refractory Multiple Myeloma (MM). Abstract #3225. American Society of Hematology, Dec. 7-11, 2001.

Zangari, M. Tricot, G., Zeldis, J., Eddlemon, P., Saghafifar, F., Barlogie, B., Results of Phase 1 Study of CC5013, for the Treatment of Multiple Myeloma (MM) Patients Who Replase After High Dose Chemotherapy (HDCT). Abstract #3226. American Society of Hematology, Dec. 7-11, 2001.

Thomas, D.A. et al., "The revitalization of thalidomide," *Annals of Oncology*, Jul. 2001, 12(7):885-886.

Bain, Barbara J., "The Relationship between the Myelodysplastic Syndromes and the Myeloproliferative Disorders," *Leukemia & Lymphoma*, 1999, 34(5-6):443-449.

Melchert, Magda, et al., "The thalidomide saga," *The International Journal of Biochemistry & Cell Biology*, Jul. 2007, 39:1489-1499.

Search Report in corresponding ARIPO Appl. No. AP/P/2006/003799 dated Mar. 3, 2009.

Sorbera, L. et al., "CC-5013. Treatment of Multiple Myeloma, Treatment of Melanoma, Treatment of Myelodysplastic Syndrome, Angiogenesis Inhibitor, TNF-α Production Inhibitor," *Drugs of the Future*, 2003, 28(5):425-431.

List, Alan F. et al., "High Erythropoietic Remitting Activity of the Immunomodulatory Thalidomide Analog, CC5013, in Patients with Myelodysplastic Syndrome (MDS)," *Blood*, 2002, 100(11):96a Abstract #353.

List, Alan F. et al., "Efficacy and Safety of CC5013 for Treatment of Anemia in Patients with Myelodysplastic Syndromes (MDS)," *Blood*, 2003, 102(11):184a Abstract #641.

Neuwirtova, R. et al., "Immunomodulatory therapy of low-risk myelodysplastic syndromes," *Onkologie*, 2000, 23(7):82 Abstract #0305.

Partial European Search Report in corresponding EP Appl. No. 04821987.7 dated Mar. 23, 2009.

Strupp, C., et al., "Thalidomide for the treatment of patients with myelodysplastic syndromes," *Leukemia*, 2002, 16(1):1-6.

\* cited by examiner

METHODS OF USING 4-(AMINO)-2-(2,6-DIOXO(3-PIPERIDLY))-ISOINDOLINE-3-DIONE FOR THE TREATMENT OF MYELODYSPLASTIC SYNDROMES

This application is a continuation application of U.S. patent application Ser. No. 11/654,550, filed Jan. 16, 2007, now U.S. Pat. No. 7,393,863, which is a divisional application of Ser. No. 10/411,649, now U.S. Pat. No. 7,189,740, which claims priority to U.S. provisional application No. 60/418,468 filed on Oct. 15, 2002, the entirety of which is incorporated herein by reference.

1. FIELD OF THE INVENTION

This invention relates to methods of treating, preventing and/or managing myelodysplastic and related syndromes which comprise the administration of immunomodulatory compounds alone or in combination with known therapeutics. The invention also relates to pharmaceutical compositions and dosing regimens. In particular, the invention encompasses the use of immunomodulatory compounds in conjunction with transplantation therapy and/or other standard therapies for myelodysplastic syndromes.

2. BACKGROUND OF THE INVENTION

2.1. Pathobiology of MDS

Myelodysplastic syndrome ("MDS") refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. *The Merck Manual* 953 (17$^{th}$ ed. 1999) and List et al., 1990, *J. Clin. Oncol.* 8:1424.

The initial hematopoietic stem cell injury can be from causes such as, but not limited to, cytotoxic chemotherapy, radiation, virus, chemical exposure, and genetic predisposition. A clonal mutation predominates over bone marrow, suppressing healthy stem cells. In the early stages of MDS, the main cause of cytopenias is increased programmed cell death (apoptosis). As the disease progresses and converts into leukemia, gene mutation rarely occurs and a proliferation of leukemic cells overwhelms the healthy marrow. The disease course differs, with some cases behaving as an indolent disease and others behaving aggressively with a very short clinical course that converts into an acute form of leukemia.

The actual incidence of MDS in the U.S. is unknown. MDS was first considered a distinct disease in 1976, and occurrence was estimated at 1500 new cases every year. At that time, only patients with less than five percent blasts were considered to have this disorder. Statistics from 1999 estimated 13,000 new cases per year and about 1000 cases per year in children, surpassing chronic lymphocytic leukemia as the most common form of leukemia in the western hemisphere. The perception that the incidence is increasing may be due to improvements in recognition and criteria for diagnosis. The disease is found worldwide.

An international group of hematologists, the French-American-British (FAB) Cooperative Group, classified MDS disorders into five subgroups, differentiating them from acute myeloid leukemia. *The Merck Manual* 954 (17$^{th}$ ed. 1999); Bennett J. M., et al., *Ann. Intern. Med.* 1985 Oct., 103(4): 620-5; and Besa E. C., *Med. Clin. North Am.* 1992 May, 76(3): 599-617. An underlying trilineage dysplastic change in the bone marrow cells of the patients is found in all subtypes.

There are two subgroups of refractory anemia characterized by five percent or less myeloblasts in bone marrow: (1) refractory anemia (RA) and; (2) RA with ringed sideroblasts (RARS), defined morphologically as having 15% erythroid cells with abnormal ringed sideroblasts, reflecting an abnormal iron accumulation in the mitochondria. Both have a prolonged clinical course and low incidence of progression to acute leukemia. Besa E. C., *Med. Clin. North Am.* 1992 May, 76(3): 599-617.

There are two subgroups of refractory anemias with greater than five percent myeloblasts: (1) RA with excess blasts (RAEB), defined as 6-20% myeloblasts, and (2) RAEB in transformation (RAEB-T), with 21-30% myeloblasts. The higher the percentage of myeloblasts, the shorter the clinical course and the closer the disease is to acute myelogenous leukemia. Patient transition from early to more advanced stages indicates that these subtypes are merely stages of disease rather than distinct entities. Elderly patients with MDS with trilineage dysplasia and greater than 30% myeloblasts who progress to acute leukemia are often considered to have a poor prognosis because their response rate to chemotherapy is lower than de novo acute myeloid leukemia patients. The World Health Organization (WHO) classification (1999) proposes to include all cases of RAEB-T, or patients with greater than 20% myeloblasts, in the category of acute leukemia because these patients have similar prognostic outcomes. However, their response to therapy is worse than the de novo or more typical acute myelogenous leukemia or acute non-lymphocytic leukemia (ANLL) patient. Id.

The fifth type of MDS, the most difficult to classify, is called chronic myelomonocytic leukemia (CMML). This subtype can have any percentage of myeloblasts but presents with a monocytosis of 1000/dL or more. It may be associated with splenomegaly. This subtype overlaps with a myeloproliferative disorder and may have an intermediate clinical course. It is differentiated from the classic chronic myelocytic leukemia (CML) that is characterized by a negative Ph chromosome. The recent WHO classification (1999) proposes that juvenile and proliferative CMML be listed separately from FAB under MDS/myeloproliferative disorder (MPD) with splenomegaly and greater than 13,000 total WBC. CMML is limited to monocytosis, less than 13,000/mm$^3$ total leukocytes, and requires trilineage dysplasia. Id. Harris N. L., et al., *J. Clin. Oncol.* 1999 Dec., 17(12): 3835-49. Finally, some other international organizations, including WHO, have suggested a sixth class of MDS patients, characterized by a del (5q) abnormality.

MDS is primarily a disease of elderly people, with the median onset in the seventh decade of life. The median age of these patients is 65 years, with ages ranging from the early third decade of life to as old as 80 years or older. The syndrome may occur in any age group, including the pediatric population. Patients who survive malignancy treatment with alkylating agents, with or without radiotherapy, have a high incidence of developing MDS or secondary acute leukemia. About 60-70% of patients do not have an obvious exposure or cause for MDS, and are classified as primary MDS patients.

The most common cases of MDS are primary, or idiopathic. However, a nonspecific history of exposure to indeterminable chemicals or radiation 10-15 years prior to onset of disease may be present in about 50% of patients. This relationship to pathogenesis remains unproved. Compounds such as, but not limited to, benzene, insecticides, weed killers, and fungicides are possible causes of MDS. Goldberg H., et al., *Cancer Res.* 1990 Nov. 1; 50(21): 6876-81. Secondary MDS describes development of MDS or acute leukemia after known exposures to chemotherapy drugs that can cause bone marrow damage. These drugs are associated with a high incidence of chromosomal abnormalities following exposure and at the time of MDS or acute leukemia diagnosis.

Further, MDS is associated with complications associated with severe cytopenias. Other complications are development of myelofibrosis, which can accelerate decline in blood counts and increase transfusion requirements. Transformation to acute leukemia accelerates the development of complications such as anemia, bleeding, and infections.

Recently, the International MDS Risk Analysis (IMRA) Workshop proposed an International Prognosis Scoring System (IPSS) to decrease imprecision in predicting survival and AML risk in MDS patients. The IPSS is based on the number of cytopenias, percentage of BM blasts, and type of cytogenetic abnormalities (Table 1). Greenberg et al., *Blood* 1997, 89:2079-88. The latter are categorized into good (normal, –Y, del (5q), del (20q)), intermediate, and poor subgroups (complex or chromosome 7 abnormalities).

TABLE 1

International Prognostic Scoring System for MDS

| Prognostic | Score Value | | | | |
|---|---|---|---|---|---|
| Variable | 0 | 0.5 | 1.0 | 1.5 | 2.0 |
| Bone marrow blasts (%) | <5 | 5-10 | — | 11-20 | 21-30 |
| Karyotype* | Good | Intermediate | Poor | | |
| Cytopenias | 0/1 | 2/3 | | | |

*Good, normal, del (5q), del (20q), –Y; Poor, complex (>3) or chromosome 7 abnormalities; Intermediate, +8, and other single or double abnormalities.

2.2. MDS Treatment

The current treatment of MDS is based on the stage and the mechanism of the disease that predominates the particular phase of the disease process. Bone marrow transplantation has been used in patients with poor prognosis or late-stage MDS. Epstein and Slease, 1985, *Surg. Ann.* 17:125. This type of therapy, however, is both painful for donor and recipient, because of the involvement of invasive procedures and can cause severe and even fatal complications to the recipient, particularly with allogeneic transplant and related Graft Versus Host Disease (GVHD) results. Therefore, the risk of GVHD restricts the use of bone marrow transplantation to patients with otherwise fatal diseases. Further, as most patients are elderly and only a few young MDS patients will have a matched donor, the use of bone marrow transplantation is limited.

An alternative approach to therapy for MDS is the use of hematopoietic growth factors or cytokines to stimulate blood cell development in a recipient. Dexter, 1987, *J. Cell Sci.* 88:1; Moore, 1991, *Annu. Rev. Immunol.* 9:159; and Besa E. C., *Med. Clin. North Am.* 1992 May, 76(3): 599-617. The process of blood cell formation, by which a small number of self-renewing stem cells give rise to lineage specific progenitor cells that subsequently undergo proliferation and differentiation to produce the mature circulating blood cells has been shown to be at least in part regulated by specific hormones. These hormones are collectively known as hematopoietic growth factors. Metcalf, 1985, *Science* 229:16; Dexter, 1987, *J. Cell Sci.* 88: 1; Golde and Gasson, 1988, *Scientific American*, July: 62; Tabbara and Robinson, 1991, *Anti-Cancer Res.* 11:81; Ogawa, 1989, *Environ. Health Presp.* 80:199; and Dexter, 1989, *Br. Med. Bull.* 45:337. The most well characterized growth factors include erythropoietin (EPO), granulocyte macrophage colony stimulating factor (GM-CSF), and granulocyte colony stimulating factor (G-CSF). Apart from inducing proliferation and differentiation of hematopoietic progenitor cells, such cytokines have also been shown to activate a number of functions of mature blood cells, including influencing the migration of mature hematopoietic cells. Stanley et al., 1976, *J. Exp. Med.* 143: 631; Schrader et al., 1981, *Proc. Natl. Acad. Sci. U.S.A.* 78:323; Moore et al., 1980, *J. Immunol.* 125:1302; Kurland et al., 1979, *Proc. Natl. Acad. Sci. U.S.A.* 76:2326; Handman and Burgess, 1979, *J. Immunol.* 122:1134; Vadas et al., 1983, *Blood* 61:1232; Vadas et al., 1983, *J. Immunol.* 130:795; and Weibart et al., 1986, *J. Immunol.* 137:3584.

Unfortunately, hematopoietic growth factors have not proven effective in many clinical settings. Clinical trials of MDS patients treated with recombinant human GM-CSF and G-CSF have shown that while these cytokines can restore granulocytopoiesis in treated patients, their efficacy is restricted to the granulocyte or monocyte lineage with little or no improvement in hemoglobin or platelet counts. Schuster et al., 1990, *Blood* 76 (Suppl.1):318a. When such patients were treated with recombinant human EPO, a sustained improvement in hemoglobin or decrease in transfusion requirement was achieved in only less than 25% of patients. Besa et al., 1990, 76 (Suppl.1): 133a; Hellstrom et al., 1990, 76 (Suppl.1):279a; Bowen et al., 1991, *Br. J. Haematol.* 77:419. Therefore, there remains a need for safe and effective methods of treating and managing MDS.

2.3. Thalidomide and Other Compounds useful in the Treatment of Disease

Thalidomide is a racemic compound sold under the tradename Thalomid® and chemically named α-(N-phthalimido) glutarimide or 2-(2,6-dioxo-3-piperidinyl)-1H-isoindole-1,3 (2H)-dione. Thalidomide was originally developed in the 1950's to treat morning sickness, but due to its teratogenic effects was withdrawn from use. Thalidomide has been approved in the United States for the acute treatment of the cutaneous manifestations of erythema nodosum leprosum in leprosy. Physicians' Desk Reference, 1154-1158 (56th ed., 2002). Because its administration to pregnant women can cause birth defects, the sale of thalidomide is strictly controlled. Id. Thalidomide has reportedly been studied in the treatment of other diseases, such as chronic graft-vs-host disease, rheumatoid arthritis, sarcoidosis, several inflammatory skin diseases, and inflammatory bowel disease. See generally, Koch, H. P., Prog. Med. Chem. 22:165-242 (1985). See also, Moller, D. R., et al., J. Immunol. 159:5157-5161 (1997); Vasiliauskas, E. A., et al., Gastroenterology 117:1278-1287 (1999); Ehrenpreis, E. D., et al., Gastroenterology 117:1271-1277 (1999). It has further been alleged that thalidomide can be combined with other drugs to treat ischemia/repercussion associated with coronary and cerebral occlusion. See U.S. Pat. No. 5,643,915, which is incorporated herein by reference.

More recently, thalidomide was found to exert immunomodulatory and anti-inflammatory effects in a variety of disease states, cachexia in AIDS, and opportunic infections in AIDS. In studies to define the physiological targets of thalidomide, the drug was found to have a wide variety of biological activities exclusive of its sedative effect including neurotoxicity, teratogenicity, suppression of TNF-α production by monocytes/macrophages and the accompanying inflammatory toxicities associated with high levels of TNF-α, and inhibition of angiogenesis and neovascularization.

Additionally, beneficial effects have been observed in a variety of dermatological conditions, ulcerative colitis, Crohn's disease, Bechets's syndrome, systemic lupus erythematosis, aphthous ulcers, and lupus. The anti-angiogenic properties of thalidomide in in vivo models have been reported. D'Amato et al., *Thalidomide Is An Inhibitor Of Angiogenesis*, 1994, *PNAS, USA* 91:4082-4085.

One of the most therapeutically significant potential uses of thalidomide is in the treatment of cancer. The compound has been investigated in the treatment of various types of cancer, such as refractory multiple myeloma, brain, breast, colon, and prostate cancer, melanoma, mesothelioma, and renal cell carcinoma. See, e.g., Singhal, S., et al., *New England J. Med.* 341(21):1565-1571 (1999); and Marx, G. M., et al., *Proc. Am. Soc. Clin. Oncology* 18:454a (1999). Thalidomide reportedly can also be used to prevent the development of chronic cardiomyopathy in rats caused by doxorubicin. Costa, P. T., et al., *Blood* 92(10: suppl. 1):235b (1998). Other reports concerning the use of thalidomide in the treatment of specific cancers include its combination with carboplatin in the treatment of glioblastoma multiforme. McCann, J., *Drug Topics* 41-42 (Jun. 21, 1999). The use of thalidomide in combination with dexamethasone reportedly was effective in the treatment of patients suffering from multiple myeloma who also received, as supportive care, human granulocyte colony-stimulating factor (G-CSF), ciprofloxacin, and non-absorbable antifungal agents. Kropff, M. H., *Blood* 96(11 part 1):168a (2000); see also, Munshi, N. et al., *Blood* 94(10 part 1):578a (1999). Other chemotherapy combinations that comprise thalidomide are disclosed in International Application No. PCT/US01/15326 to R. Govindarjan and A. Zeitlan, and in International Application No. PCT/US01/15327 to J. B. Zeldis, et al.

In an effort to provide compounds that have greater therapeutic safety and efficacy than thalidomide, researchers have begun investigating a large number of other compounds, some of which are derivatives of thalidomide. See, e.g., Marriott, J. B., et al., *Expert Opin. Biol. Ther.* 1(4):1-8 (2001); G. W. Muller, et al., Journal of Medicinal Chemistry 39(17): 3238-3240 (1996); and G. W. Muller, et al., Bioorganic & Medicinal Chemistry Letters 8: 2669-2674 (1998). Examples include, but are not limited to, the substituted 2-(2,6-dioxopiperidin-3-yl) phthalimies and substituted 2-(2,6-dioxopiperidin-3-yl)-1-oxoisoindoles described in U.S. Pat. Nos. 6,281,230 and 6,316,471, both to G. W. Muller, et al.

A group of compounds selected for their capacity to potently inhibit TNF-α production by LPS stimulated PBMC has been investigated. L. G. Corral, et al., Ann. Rheum. Dis. 58: (Suppl 1) 1107-1113 (1999). These compounds, which are referred to as IMiDs™ or Immunomodulatory Drugs, show not only potent inhibition of TNF-α but also marked inhibition of LPS induced monocyte IL1β and IL12 production. LPS induced IL6 is also inhibited by IMiDs™, albeit partially. These compounds are potent stimulators of LPS induced IL10, increasing IL10 levels by 200 to 300%. Id.

While many such compounds have shown promise as therapeutic agents, their mechanisms of action and effectiveness are still under investigation. Moreover, there remains a need for therapeutic agents to treat MDS and its related disorders.

3. SUMMARY OF THE INVENTION

This invention encompasses methods of treating or preventing myelodysplastic syndrome ("MDS") which comprise administering to a patient in need thereof a therapeutically or prophylactically effective amount of an immunomodulatory compound of the invention or a pharmaceutically acceptable salt, solvate, hydrate, stereoisomer, clathrate, or prodrug thereof. The invention also encompasses methods of managing MDS (e.g., lengthening the time of remission) which comprise administering to a patient in need of such management a therapeutically or prophylactically effective amount of an immunomodulatory compound of the invention, or a pharmaceutically acceptable salt, solvate, hydrate, stereoisomer, clathrate, or prodrug thereof.

One embodiment of the invention encompasses the use of one or more immunomodulatory compounds in combination with conventional therapies presently used to treat, prevent or manage MDS such as hematopoietic growth factors, cytokines, cancer chemotherapeutics, stem cell transplantation and other transplantations.

The invention further encompasses pharmaceutical compositions, single unit dosage forms, and kits suitable for use in treating, preventing and/or managing MDS, which comprise an immunomodulatory compound of the invention, or a pharmaceutically acceptable salt, solvate, hydrate, stereoisomer, clathrate, or prodrug thereof.

4. DETAILED DESCRIPTION OF THE INVENTION

A first embodiment of the invention encompasses methods of treating or preventing MDS which comprise administering to a patient in need of such treatment or prevention a therapeutically or prophylactically effective amount of an immunomodulatory compound, or a pharmaceutically acceptable salt, solvate, hydrate, stereoisomer, clathrate, or prodrug thereof. The embodiment encompasses the treatment, prevention or management of specific sub-types of MDS such as refractory anemia, refractory anemia with ringed sideroblasts, refractory anemia with excess blasts, refractory anemia with excess blasts in transformation and chronic myelomonocytic leukemia.

As used herein, the term "myelodysplastic syndromes" or "MDS" means hematopoietic stem cell disorders characterized by one or more of the following: ineffective blood cell production, progressive cytopenias, risk of progression to acute leukemia or cellular marrow with impaired morphology and maturation (dysmyelopoiesis). The term "myelodysplastic syndromes" or "MDS" unless otherwise noted includes: refractory anemia, refractory anemia with ringed sideroblasts, refractory anemia with excess blasts, refractory anemia with excess blasts in transformation and chronic myelomonocytic leukemia.

Another embodiment of the invention encompasses methods of managing MDS which comprises administering to a patient in need of such management a prophylactically effective amount of an immunomodulatory compound, or a pharmaceutically acceptable salt, solvate, hydrate, stereoisomer, clathrate, or prodrug thereof.

Another embodiment of the invention encompasses a pharmaceutical composition comprising an immunomodulatory compound, or a pharmaceutically acceptable salt, solvate, hydrate, stereoisomer, clathrate, or prodrug thereof.

Also encompassed by the invention are single unit dosage forms comprising an immunomodulatory compound, or a pharmaceutically acceptable salt, solvate, hydrate, stereoisomer, clathrate, or prodrug thereof.

Another embodiment of the invention encompasses a kit comprising: a pharmaceutical composition comprising an immunomodulatory compound, or a pharmaceutically acceptable salt, solvate, hydrate, stereoisomer, clathrate, or prodrug thereof and a second active or dexamethasone or instructions for use. The invention further encompasses kits comprising single unit dosage forms.

One embodiment of the invention encompasses a method of treating, preventing and/or managing MDS, which comprises administering to a patient in need of such treatment, prevention and/or management a therapeutically or prophylactically effective amount of an immunomodulatory compound, or a pharmaceutically acceptable salt, solvate, hydrate, stereoisomer, clathrate, or prodrug thereof, and a therapeutically or prophylactically effective amount of a second active agent.

The second active agent is preferably a hematopoietic growth factor, a cytokine, an anti-cancer agent, an antibiotic, an anti-fungal, an anti-inflammatory, an immunosuppressive agent such as a cyclosporin, conventional therapy for MDS, or other chemotherapeutic agent found for example in the Physician's Desk Reference 2002. Preferred anti-cancer or cancer chemotherapeutics are apoptosis inducing agents, topoisomerase inhibitors, anti-angiogenesis compounds, microtubule stabilizing agents, alkylating agents and other known conventional cancer chemotherapy. Most preferred second active agents are those capable of affecting or improving blood production. Second active agents can be large molecules (e.g., proteins) or small molecules (e.g., synthetic inorganic, organometallic, or organic molecules). The examples of specific second active agent include, but are not limited to, etanercept (Enbrel®), imatinib (Glivec®), anti-TNF-α antibodies, infliximab (Remicade®), G-CSF, GM-CSF, EPO, topotecan, irinotecan, pentoxifylline, ciprofloxacin, dexamethasone, IL2, IL8, IL18, Ara-C, vinorelbine, vinblastine, isotretinoin, and 13-cis-retinoic acid. This invention also encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001). Vaccines that cause the secretion of proteins disclosed herein as well as pharmacologically active mutants, derivatives, and fusion thereof are also encompassed by the invention.

Without being limited by theory, it is believed that certain immunomodulatory compounds and proteins can act in complementary or synergistic ways in the treatment or management of MDS. It is also believed that certain proteins may reduce or eliminate particular adverse effects associated with some immunomodulatory compounds, thereby allowing the administration of larger amounts of an immunomodulatory compound to patients and/or increasing patient compliance. It is further believed that some immunomodulatory compounds may reduce or eliminate particular adverse effects associated with some protein-based MDS therapies, thereby allowing the administration of larger amounts of protein to patients and/or increasing patient compliance.

Another embodiment of the invention encompasses a method of reversing, reducing or avoiding an adverse effect associated with the administration of a chemotherapeutics or therapeutics used to treat cancer or MDS in a patient suffering from MDS, which comprises administering to a patient in need thereof a therapeutically or prophylactically effective amount of an immunomodulatory compound, or a pharmaceutically acceptable salt, solvate, hydrate, stereoisomer, clathrate, or prodrug thereof.

As inevitable leukemic transformation develops in certain stages of MDS, transplantation of peripheral blood stem cells, hematopoietic stem cell preparation or bone marrow may be necessary. It is believed that the combined use of an immunomodulatory compound and transplantation of stem cells in a patient suffering from MDS provides a unique and unexpected synergism. In particular, without being limited by theory, it is believed that an immunomodulatory compound exhibits immunomodulatory activity that may provide additive or synergistic effects when given concurrently with transplantation therapy. Immunomodulatory compounds can work in combination with transplantation therapy reducing complications associated with the invasive procedure of transplantation and risk of related Graft Versus Host Disease (GVHD). Therefore, this invention encompasses a method of treating, preventing and/or managing MDS, which comprises administering to a patient (e.g., a human) an immunomodulatory compound, or a pharmaceutically acceptable salt, solvate, hydrate, stereoisomer, clathrate, or prodrug thereof, before, during, or after transplantation therapy.

The invention also encompasses pharmaceutical compositions, single unit dosage forms, and kits which comprise one or more immunomodulatory compounds, or a pharmaceutically acceptable salt, solvate, hydrate, stereoisomer, clathrate, or prodrug thereof, a second active ingredient, and/or blood or cells for transplantation therapy. For example, the kit may contain one or more compounds of the invention, stem cells for transplantation and an immunosuppressive agent, antibiotic or other drug, each of which is to be used to treat the MDS patient.

4.1. Immunomodulatory Compounds

Compounds used in the invention include immunomodulatory compounds that are racemic, stereomerically enriched or stereomerically pure, and pharmaceutically acceptable salts, solvates, hydrates, stereoisomers, clathrates, and prodrugs thereof. Preferred compounds used in the invention are small organic molecules having a molecular weight less than about 1000 g/mol, and are not proteins, peptides, oligonucleotides, oligosaccharides or other macromolecules.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein and unless otherwise indicated, the term "immunomodulatory compounds" or "IMiDs™" (Celgene Corporation) used herein encompasses small organic molecules that markedly inhibit TNF-α, LPS induced monocyte IL1β and IL12, and partially inhibit IL6 production. Specific immunomodulatory compounds of the invention are discussed below.

TNF-α is an inflammatory cytokine produced by macrophages and monocytes during acute inflammation. TNF-α is responsible for a diverse range of signaling events within cells. TNF-α may play a pathological role in cancer. Without being limited by particular theory, one of the biological effects exerted by the immunomodulatory compounds of the invention is the reduction of synthesis of TNF-α. Immunomodulatory compounds of the invention enhance the degradation of TNF-α mRNA.

Further, without being limited by particular theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties, and efficiently co-stimulate T cells.

Specific examples of immunomodulatory compounds of the invention, include, but are not limited to, cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. No. 5,874,448; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide and EM-12), including, but not limited to, those disclosed in U.S. Pat. No. 5,635,517; and a class of non-polypeptide cyclic amides disclosed in U.S. Pat. Nos. 5,698,579 and 5,877,200; analogs and derivatives of thalidomide, including hydrolysis products, metabolites, derivatives and precursors of thalidomide, such as those described in U.S. Pat. Nos. 5,593,990, 5,629,327, and 6,071,948 to D'Amato; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents identified herein are incorporated herein by reference. Immunomodulatory compounds of the invention do not include thalidomide.

Other specific immunomodulatory compounds of the invention include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein. These compounds have the structure I:

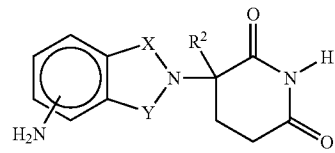

in which one of X and Y is C=O, the other of X and Y is C=O or $CH_2$, and $R^2$ is hydrogen or lower alkyl, in particular methyl. Specific immunomodulatory compounds include, but are not limited to:

1-oxo-2-(2,6-dioxopiperidin-3-yl)-4-aminoisoindoline;
1-oxo-2-(2,6-dioxopiperidin-3-yl)-5-aminoisoindoline;
1-oxo-2-(2,6-dioxopiperidin-3-yl)-6-aminoisoindoline;
1-oxo-2-(2,6-dioxopiperidin-3-yl)-7-aminoisoindoline;
1,3-dioxo-2-(2,6-dioxopiperidin-3-yl)-4-aminoisoindoline;
and 1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein. Compounds representative of this class are of the formulas:

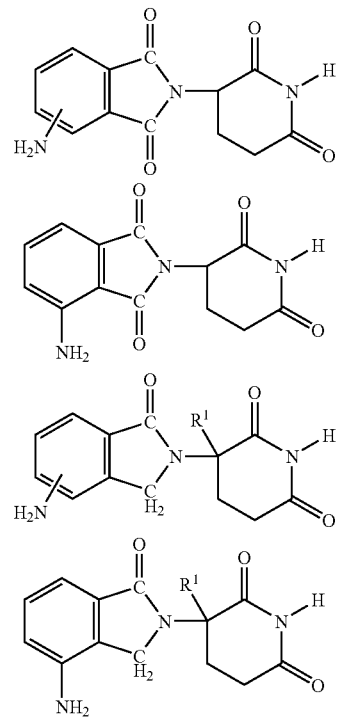

wherein $R^1$ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. patent application Ser. Nos. 10/032,286 and 09/972,487, and International Application No. PCT/US01/50401 (International Publication No. WO 02/059106), each of which are incorporated herein by reference. Representative compounds are of formula II:

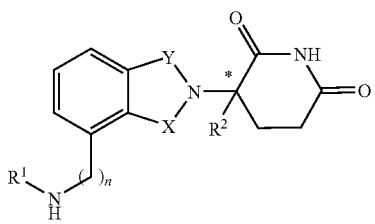

and pharmaceutically acceptable salts, hydrates, solvates, clathrates, enantiomers, diastereomers, racemates, and mixtures of stereoisomers thereof, wherein:
  one of X and Y is C=O and the other is $CH_2$ or C=O;
  $R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;
  $R^2$ is H, F, benzyl, $(C_1-C_8)$alkyl, $(C_2-C_8)$alkenyl, or $(C_2-C_8)$alkynyl;
  $R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$(O)OR^5$, $(C_1-C_8)$alkyl-$O(CO)R^5$, or $C(O)OR^5$;
  $R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;
  $R^5$ is $(C_1-C_8)$alkyl, $(C_2-C_8)$alkenyl, $(C_2-C_8)$alkynyl, benzyl, aryl, or $(C_2-C_5)$heteroaryl;
  each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O-R^5$ or the $R^6$ groups can join to form a heterocycloalkyl group;
  n is 0 or 1; and
  * represents a chiral-carbon center.
  In specific compounds of formula II, when n is 0 then R1 is (C3-C7)cycloalkyl, (C2-C8)alkenyl, (C2-C8)alkynyl, benzyl, aryl, (C0-C4)alkyl-(C1-C6)heterocycloalkyl, (C0-C4)alkyl-(C2-C5)heteroaryl, C(O)R3, C(O)OR4, (C1-C8)alkyl-N(R6)2, (C1-C8)alkyl-$OR^5$, (C1-C8)alkyl-C(O)OR5, C(S)NHR3, or (C1-C8)alkyl-O(CO)R5;
  $R^2$ is H or $(C_1-C_8)$alkyl; and
  $R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6)$heterocycloalkyl, $(C_0-C_4)$alkyl-$C_2-C_5)$heteroaryl, $(C_5-C_8)$alkyl-N$(R^6)_2$; $(C_0-C_8)$alkyl-NH—C(O)O—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables have the same definitions.
  In other specific compounds of formula II, $R^2$ is H or $(C_1-C_4)$alkyl.

In other specific compounds of formula II, $R^1$ is $(C_1-C_8)$ alkyl or benzyl.
In other specific compounds of formula II, $R^1$ is H$(C_1-C_8)$ alkyl, benzyl, $CH_2OCH_3$, $CH_2CH_2OCH_3$, or

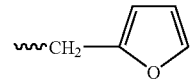

In another embodiment of the compounds of formula II, $R^1$ is

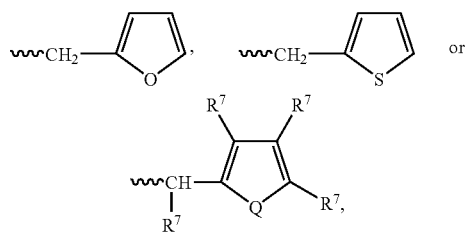

wherein Q is O or S, and each occurrence of $R^7$ is independently H, $(C_1-C_8)$alkyl, benzyl, $CH_2OCH_3$, or $CH_2CH_2OCH_3$.
In other specific compounds of formula II, $R^1$ is $C(O)R^3$.
In other specific compounds of formula II, $R^3$ is $(C_0-C_4)$ alkyl-$C_2-C_5)$heteroaryl, $(C_1-C_8)$alkyl, aryl, or $(C_0-C_4)$alkyl-$OR^5$.
In other specific compounds of formula II, heteroaryl is pyridyl, furyl, or thienyl.
In other specific compounds of formula II, $R^1$ is $C(O)OR^4$.
In other specific compounds of formula II, the H of C(O) NHC(O) can be replaced with $(C_1-C_4)$alkyl, aryl, or benzyl.

Still other specific immunomodulatory compounds of the invention belong to a class of isoindole-imides disclosed in U.S. patent application Ser. No. 09/781,179, International Publication No. WO 98/54170, and U.S. Pat. No. 6,395,754, each of which are incorporated herein by reference. Representative compounds are of formula III:

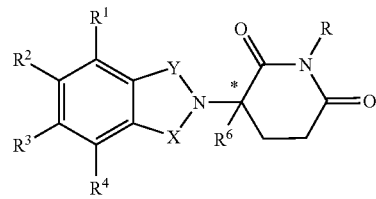

and pharmaceutically acceptable salts, hydrates, solvates, clathrates, enantiomers, diastereomers, racemates, and mixtures of stereoisomers thereof, wherein:
  one of X and Y is C=O and the other is $CH_2$ or C=O;
  R is H or CH2OCOR';
  (i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;
  $R^5$ is hydrogen or alkyl of 1 to 8 carbons
  $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_nH_2n)$— in which n has a value of 0 to 4;

each of R8 and R9 taken independently of the other is hydrogen or alkyl of 1 to 8 carbon atoms, or R8 and R9 taken together are tetramethylene, pentamethylene, hexamethylene, or —$CH_2CH_2[X]X_1CH_2CH_2$— in which $[X]X_1$ is —O—, —S—, or —NH—;

$R^{10}$ is hydrogen, alkyl of to 8 carbon atoms, or phenyl; and
* represents a chiral-carbon center.

The most preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635, 517, incorporated herein by reference). The compounds are available from Celgene Corporation, Warren, N.J. 4-(Amino)-2-(2,6-dioxo(3-piperidyl))-isoindoline-1,3-dione (ACTIMID™) has the following chemical structure:

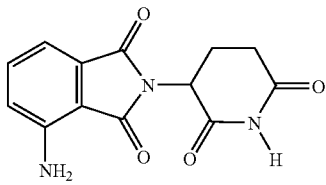

3-(4-amino-1-oxo-1,3-dihydro-isoindol-2-yl)-piperidine-2,6-dione (REVIMID™) has the following chemical structure:

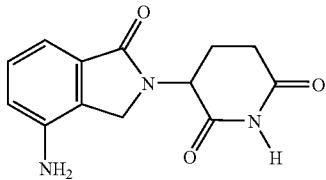

The compounds of the invention can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —$NO_2$, —ONO, or —$ONO_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elselvier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2. Second Active Agents

One or more second active ingredients can be used in the methods and compositions of the invention together with an immunomodulatory compound of the invention. In a preferred embodiment, the second active agents are capable of affecting or improving the process of blood cell production. Specific second active agents also stimulate the division and differentiation of committed erythroid progenitors in cells in vitro or in vivo.

Second active agents can be large molecules (e.g., proteins) or small molecules (e.g., synthetic inorganic, organometallic, or organic molecules). The second active agents include but are not limited to hematopoietic growth factors, cytokines, anti-cancer agents, antibiotics, proteasome inhibitors, immunosuppressive agents and other therapeutics discussed herein. Particular agents include, but are not limited to, G-CSF, GM-CSF, EPO, dexamethasone, topotecan, pentoxifylline, irinotecan, ciprofloxacin, vinorelbine, IL2, IL8, IL18, Ara-C, isotretinoin, 13-cis-retinoic acid, 12-O-tetradecanoylphorbol-13-acetate (TPA), 5-AZA2'-deoyxcytidine, 9-nitrocamptothecin, transretinoic acid, amifostine, amphotericin B and liposomal amphotericin B, anti-CD-20 monoclonal antibody, anti-thymocyle globulin (ATG), arsenic trioxide, azacytidine, bevacizumab, bismuth monoclonal antibody, bryostatin, busulfan, caspofungin acetate, celocoxib, cladribine, cyclophosphamide, cyclosporine, cytarabine, cytosine, daunorubicin, depsipeptide, etoposide, farresy transferase inhibitor, flavopiridol, Flt3 ligand, fludarabine, gentuzumab ozogomicin (mylotarg), etanercept (Enbrel®), imatinib (Glivec®), anti-TNF-α antibodies, infliximab (Remicade®), humanized monoclonal anti-VEGF antibody, idarubicine, leucovorin, melphalan, mitoxantrone, monoclonal antibody ABX-CBL, monoclonal antibody CD52, mycophenolate mofetil, oblimersen, omega-3 fatty acids, pentostatin, phenylbutyrate, PR1 leukemia peptide vaccine, montanide, proteasome inhibitor, sodium phenyl-butyrate, sodium salicylate, temozolomide, thymoglobulin, troxatyl, tumor necrosis factor receptor IgG chimera, Yttrium Y 90 humanized monoclonal antibody M195. In a specific embodiment of the invention, an immunomodulatory compound of the invention is used in combination with pentoxifylline, ciprofloxacin, and/or dexamethasone.

This invention also encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Recombinant and mutated forms of G-CSF can be prepared as described in U.S. Pat. Nos. 4,810,643; 4,999,291; 5,528,823; and 5,580,755; all of which are incorporated herein by reference. Recombinant and mutated forms of GM-CSF can be prepared as described in U.S. Pat. Nos. 5,391,485; 5,393,870; and 5,229,496; all of which are incorporated herein by reference. In fact, recombinant forms of G-CSF and GM-CSF are currently sold in the United States for the treatment of symptoms associated with specific chemotherapies. A recombinant form of G-CSF known as filgrastim is sold in the United States under the trade name NEUPOGEN®. NEUPOGEN® is known to stimulate division and maturation of granulocytes, mostly neutrophils, in MDS patients and to enhance erythroid response in combination with EPO. *Physicians' Desk Reference*, 587-592 (56th ed., 2002). A recombinant form of GM-CSF known as sargramostim is also sold in the United States under the trade name LEUKINE®. LEUKINE® is known to stimulate division and maturation of earlier myeloid and macrophage precursor cells and has been reported to increase granulocytes. *Physicians' Desk Reference*, 1755-1760 (56th ed., 2002). A recombinant form of EPO known as epoetin alfa is sold in the United States under the trade name EPOGEN®. EPOGEN® is used to stimulate red cell production by stimulating division and maturation of committed red cell precursor cells. EPOGEN® has been reported to be effective in 20-26% of MDS patient when administered by itself and in as many as 48% of patients when combined with G-CSF or GM-CSF. *Physicians' Desk Reference*, 582-587 (56th ed., 2002).

A growth-factor or cytokine such as G-CSF, GM-CSF and EPO can also be administered in the form of a vaccine. For example, vaccines that secrete, or cause the secretion of, cytokines such as G-CSF and GM-CSF can be used in the methods, pharmaceutical compositions, and kits of the invention. See, e.g., Emens, L. A., et al., *Curr. Opinion Mol. Ther.* 3(1):77-84 (2001).

Other compounds that can be administered or used in combination with an immunomodulatory compound of the invention include those disclosed in U.S. provisional patent application No. 60/380,842, filed May 17, 2002, and U.S. provisional patent application No. 60/380,843, filed May 17, 2002, both of which are incorporated herein by reference.

4.3. Methods of Treatment and Management

Methods of this invention encompass methods of preventing, treating and/or managing various types of MDS. As used herein, unless otherwise specified, the term "preventing" includes but is not limited to, inhibition or the averting of symptoms associated with MDS. The symptoms associated with MDS include, but are not limited to, anemia, thrombocytopenia, neutropenia, cytopenia, bicytopenia (two deficient cell lines), and pancytopenia (three deficient cell lines). As used herein, unless otherwise specified, the term "treating" refers to the administration of a composition after the onset of symptoms of MDS, whereas "preventing" refers to the administration prior to the onset of symptoms, particularly to patients at risk of MDS. As used herein and unless otherwise indicated, the term "managing" encompasses preventing the recurrence of MDS in a patient who had suffered from MDS, lengthening the time a patient who had suffered from MDS remains in remission, and/or preventing the occurrence of MDS in patients at risk of suffering from MDS.

The invention encompasses methods of treating or preventing patients with primary and secondary MDS. It further encompasses methods treating patients who have been previously treated for MDS, as well as those who have not previously been treated for MDS. Because patients with MDS have heterogenous clinical manifestations and varying clinical outcomes, it has become apparent that staging the patients according to their prognosis and approaching therapy depending on the severity and stage is necessary. Indeed, the methods and compositions of this invention can be used in various stages of treatments for patients with one or more types of MDS including, but not limited to, refractory anemia (RA), RA with ringed sideroblasts (RARS), RA with excess blasts (RAEB), RAEB in transformation (RAEB-T), or chronic myelomonocytic leukemia (CMML). The invention also contemplates treating patients diagnosed using the IPSS for MDS discussed above. Greenberg et al., *Blood* 1997 (89): 2079-88.

Methods encompassed by this invention comprise administering an immunomodulatory compound of the invention, or a pharmaceutically acceptable salt, solvate, hydrate, stereoisomer, clathrate, or prodrug thereof to a patient (e.g., a human) suffering, or likely to suffer, from MDS. Specific patient populations include the elderly, i.e., ages 60 and above as well as those over 35 years of age. Patients with familial history of MDS or leukemia are also preferred candidates for preventive regimens.

In one embodiment of the invention, an immunomodulatory compound of the invention is administered orally and in a single or divided daily doses in an amount of from about 0.10 to about 150 mg/day. In a particular embodiment, 4-(amino)-2-(2,6-dioxo(3-piperidyl))-isoindoline-1,3-dione (Actimid™) is administered in an amount of from about 0.1 to about 1 mg per day, or alternatively about 5 mg every other day. 3-(4-amino-1-oxo-1,3-dihydro-isoindol-2-yl)-piperidine-2,6-dione (Revimid™) can be preferably administered in an amount of from about 5 to 25 mg per day, or alternatively from about 25 to about 50 mg every other day.

4.3.1 Combination Therapy with a Second Active Agent

Particular methods of the invention comprise comprises administering 1) an immunomodulatory compound of the invention, or a pharmaceutically acceptable salt, solvate, hydrate, stereoisomer, clathrate, or prodrug thereof, and 2) a second active agent or active ingredient. Examples of immunomodulatory compounds of the invention are disclosed herein (see, e.g., section 4.1); and examples of the second active agents are also disclosed herein (see, e.g., section 4.2).

Administration of the immunomodulatory compounds and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for an immunomodulatory compound is oral. Preferred routes of administration for the second active agents or ingredients of the invention are known to those of ordinary skill in the art. See, e.g., *Physicians' Desk Reference,* 1755-1760 (56$^{th}$ ed., 2002).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of MDS being treated or managed, the severity and stage of MDS, and the amount(s) of immunomodulatory compounds of the invention and any optional additional active agents concurrently administered to the patient. In a particular embodiment, the second active agent is GM-CSF, G-CSF, EPO, transretinoic acid, dexamethasone, topotecan, pentoxifylline, ciprofloxacin, dexamethasone, IL2, IL8, IL18, Ara-C, vinorelbine, or a combination thereof. GM-CSF is administered in an amount of from about 60 to about 500 mcg/m$^2$ intravenously over 2 hours, or from about 5 to about 12 mcg/m$^2$/day subcutaneously. G-CSF is administered subcutaneously in an amount of about 1 mcg/kg/day initially and can be adjusted depending on rise of total granulocyte counts. The maintenance dose is 300 (in smaller patients) or 480 mcg subcutaneously. EPO is administered subcutaneously in an amount of 10,000 Unit 3 times per week.

4.3.2 Use with Transplantation Therapy

In still another embodiment, this invention encompasses a method of treating, preventing and/or managing MDS, which comprises administering the immunomodulatory compound of the invention, or a pharmaceutically acceptable salt, solvate, hydrate, stereoisomer, clathrate, or prodrug thereof, in conjunction with transplantation therapy. As discussed elsewhere herein, the treatment of MDS is based on the stages and mechanism of the disease. As inevitable leukemic transformation develops in certain stages of MDS, transplantation of peripheral blood stem cells, hematopoietic stem cell preparation or bone marrow may be necessary. The combined use of the immunomodulatory compound of the invention and transplantation therapy provides a unique and unexpected synergism. In particular, an immunomodulatory compound of the invention exhibits immunomodulatory activity that may provide additive or synergistic effects when given concurrently with transplantation therapy in patients with MDS. An immunomodulatory compound of the invention can work in combination with transplantation therapy reducing complications associated with the invasive procedure of transplantation and risk of related Graft Versus Host Disease (GVHD). This invention encompasses a method of treating, preventing and/or managing MDS which comprises administering to a patient (e.g., a human) an immunomodulatory compound of the invention, or a pharmaceutically acceptable salt, solvate, hydrate, stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods of the invention are disclosed in U.S. provisional patent application No. 60/372,348, filed Apr. 12, 2002 by R. Hariri et al., the entirety of which is incorporated herein by reference.

4.3.3. Cycling Therapy

In certain embodiments, the prophylactic or therapeutic agents of the invention are cyclically administered to a patient. Cycling therapy involves the administration of a first agent for a period of time, followed by the administration of the agent and/or the second agent for a period of time and repeating this sequential administration. Cycling therapy can reduce the development of resistance to one or more of the therapies, avoid or reduce the side effects of one of the therapies, and/or improves the efficacy of the treatment.

In a particular embodiment, prophylactic or therapeutic agents are administered in a cycle of about 16 weeks, about once or twice every day. One cycle can comprise the administration of a therapeutic or prophylactic agent and at least one (1) or three (3) weeks of rest. The number of cycles administered is from about 1 to about 12 cycles, more typically from about 2 to about 10 cycles, and more typically from about 2 to about 8 cycles.

4.4. Pharmaceutical Compositions and Single Unit Dosage Forms

Pharmaceutical compositions can be used in the preparation of individual, single unit dosage forms. Pharmaceutical compositions and dosage forms of the invention comprise an immunomodulatory compound of the invention, or a pharmaceutically acceptable salt, solvate, hydrate, stereoisomer, clathrate, or prodrug thereof. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active ingredients disclosed herein (e.g., an immunomodulatory compound of the invention, or a pharmaceutically acceptable salt, solvate, hydrate, stereoisomer, clathrate, or prodrug thereof, and a second active ingredient). Examples of optional additional active ingredients are disclosed herein (see, e.g., section 4.2).

Single unit dosage forms of the invention are suitable for oral, mucosal (e.g., nasal, sublingual, vaginal, buccal, or rectal), or parenteral (e.g., subcutaneous, intravenous, bolus injection, intramuscular, or intraarterial), transdermal or transcutaneous administration to a patent. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an immunomodulatory compound of the invention, or a pharmaceutically acceptable salt, solvate, hydrate, stereoisomer, clathrate, or prodrug thereof in an amount of from about 0.10 to about 150 mg. Typical dosage forms comprise an immunomodulatory compound of the invention, or a pharmaceutically acceptable salt, solvate, hydrate, stereoisomer, clathrate, or prodrug thereof in an amount of about 0.1, 1, 2, 5, 7.5, 10, 12.5, 15, 17.5, 20, 25, 50, 100, 150 or 200 mg. In a particular embodiment, a preferred dosage form comprises 4-(amino)-2-(2,6-dioxo(3-piperidyl))-isoindoline-1,3-dione (Actimid™) in an amount of about 1, 2, 5, 10, 25 or 50 mg. In a specific embodiment, a preferred dosage form comprises 3-(4-amino-1-oxo-1,3-dihydro-isoindol-2-yl)-piperidine-2,6-dione (Revimid™) in an amount of about 5, 10, 25 or 50 mg. Typical dosage forms comprise the second active ingredient in an amount of 1 to about 1000 mg, from about 5 to about 500 mg, from about 10 to about 350 mg, or from about 50 to about 200 mg. Of course, the specific amount of the second active ingredient will depend on the specific agent used, the type of MDS being treated or managed, and the amount(s) of immunomodulatory compounds of the invention, and any optional additional active agents concurrently administered to the patient.

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an immunomodulatory compound of the invention, anhydrous lactose, microcrystalline cellulose, polyvinylpyrrolidone, stearic acid, colloidal anhydrous silica, and gelatin.

4.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention, and its derivatives. See, e.g., U.S. Pat. No. 5,134,127, which is incorporated herein by reference.

4.4.4 Topical and Mucosal Dosage Forms

Topical and mucosal dosage forms of the invention include, but are not limited to, sprays, aerosols, solutions, emulsions, suspensions, or other forms known to one of skill in the art. See, e.g., *Remington's Pharmaceutical Sciences*, $16^{th}$ and $18^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.5 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of an immunomodulatory compound of the invention, or a pharmaceutically acceptable salt, solvate, hydrate, stereoisomer, prodrug, or clathrate thereof. Kits encompassed by this invention can further comprise additional active ingredients such as G-CSF, GM-CSF, EPO, topotecan, pentoxifylline, ciprofloxacin, dexamethasone, IL2, IL8, IL18, Ara-C, vinorelbine, isotretinoin, 13-cis-retinoic acid, or a pharmacologically active mutant or derivative thereof, or a combination thereof. Examples of the additional active ingredients include, but are not limited to, those disclosed herein (see, e.g., section 4.2).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

The following studies are intended to further illustrate the invention without limiting its scope.

Excessive production of the growth inhibitory cytokine TNF-α is demonstrated in bone marrow plasma of patients with MDS, implicating TNF-α as a critical negative regulator of erythroid progenitor survival in the disorder. As a result, a study with an immunomodulatory compound of the invention was conducted.

5.1. Pharmacology and Toxicology Studies

A series of non-clinical pharmacology and toxicology studies have been performed to support the clinical evaluation of an immunomodulatory compound of the invention in human subjects. These studies were performed in accordance with internationally recognized guidelines for study design and in compliance with the requirements of Good Laboratory Practice (GLP), unless otherwise noted.

The pharmacological properties of 3-(4-amino-1-oxo-1,3-dihydro-isoindol-2-yl)-piperidine-2,6-dione, including activity comparisons with thalidomide, have been characterized in in vitro studies. Studies examined the effects of 3-(4-amino-1-oxo-1,3-dihydro-isoindol-2-yl)-piperidine-2,6-dione or thalidomide on the production of various cytokines. In all studies, 3-(4-amino-1-oxo-1,3-dihydro-isoindol-2-yl)-piperidine-2,6-dione was at least 50 times more potent than thalidomide. In addition, a safety pharmacology study of 3-(4-amino-1-oxo-1,3-dihydro-isoindol-2-yl)-piperidine-2,6-dione has been conducted in dogs and the effects of 3-(4-amino-1-oxo-1,3-dihydro-isoindol-2-yl)-piperidine-2,6-dione on ECG parameters were examined further as part of three repeat-dose toxicity studies in primates. The results of these studies are described below.

5.2. Modulation of Cytokine Production

Inhibition of TNF-α production following LPS-stimulation of human PBMC and human whole blood by 3-(4-amino-1-oxo-1,3-dihydro-isoindol-2-yl)-piperidine-2,6-dione or thalidomide was investigated in vitro (Muller et al., *Bioorg. Med. Chem. Lett.* 9:1625-1630, 1999). The $IC_{50}$'s of 3-(4-amino-1-oxo-1,3-dihydro-isoindol-2-yl)-piperidine-2,6-dione for inhibiting production of TNF-α following LPS-stimulation of PBMC and human whole blood were ~100 nM (25.9 ng/mL) and ~480 nM (103.6 ng/mL), respectively. Thalidomide, in contrast, had an $IC_{50}$ of ~194 μM (50.2 μg/mL) for inhibiting production of TNF-α following LPS-stimulation of PBMC.

In vitro studies suggest a pharmacological activity profile for 3-(4-amino-1-oxo-1,3-dihydro-isoindol-2-yl)-piperidine-2,6-dione that is similar to, but 50 to 2000 times more potent than, thalidomide. The pharmacological effects of 3-(4-amino-1-oxo-1,3-dihydro-isoindol-2-yl)-piperidine-2,6-dione derive from its action as an inhibitor of cellular response to receptor-initiated trophic signals (e.g., IGF-1, VEGF, cyclooxygenase-2), and other activities. As a result, 3-(4-amino-1-oxo-1,3-dihydro-isoindol-2-yl)-piperidine-2,6-dione suppresses the generation of inflammatory cytokines, down-regulates adhesion molecules and apoptosis inhibitory proteins (e.g., cFLIP, cIAP), promotes sensitivity to death-receptor initiated programmed cell death, and suppresses angiogenic response. The studies show that 3-(4-amino-1-oxo-1,3-dihydro-isoindol-2-yl)-piperidine-2,6-dione abrogates mitogenic response to VEGF in AML cells by extinguishing ligand-induced Akt-phosphorylation, and selectively suppresses MDS vs normal bone marrow progenitor formation in pre-clinical models.

5.3. Clinical Studies in MDS Patients

Protocol

An immunomodulatory compound of the invention, such as 4-(amino)-2-(2,6-dioxo(3-piperidyl))-isoindoline-1,3-dione and 3-(4-amino-1-oxo-1,3-dihydro-isoindol-2-yl)-piperidine-2,6-dione, is administered in an amount of from about 0.1 to about 25 mg per day to patients with MDS for 16 weeks, who are subsequently evaluated for a hematological response. Response rates are assessed in cohorts stratified by the likelihood of an MDS subtype to transform to leukemia according to the International Prognostic Scoring System (IPSS)-defined risk groups (i.e., IPSS Low and Intermediate I; versus IPSS Intermediate II and High).

For example, fifteen patients are enrolled in the first cohort and receive treatment with 25 mg per day of 3-(4-amino-1-oxo-1,3-dihydro-isoindol-2-yl)-piperidine-2,6-dione. The number of patients who subsequently experience an erythroid response (major or minor response) by week 16 is evaluated. If no responses are observed, the study is terminated due to lack of efficacy. If, however, 4 or more patients respond, the study is terminated due to promising clinical activity. In the intermediate case (e.g., 1, 2 or 3 patients respond), a second cohort of 10 patients is enrolled. If after the completion of treatment by the second cohort, 4 or more patients respond among the 25 patients treated, it is concluded that the 3-(4-amino-1-oxo-1,3-dihydro-isoindol-2-yl)-piperidine-2,6-dione shows promising clinical activity.

Clinical Study

Clinical studies were performed for the remitting potential of 3-(4-amino-1-oxo-1,3-dihydro-isoindol-2-yl)-piperidine-2,6-dione in MDS patients with red blood cell transfusion-dependence (>4 units/8 weeks) or symptomatic anemia (Hgb<10 g/dl). Patients received continuous treatment with 3-(4-amino-1-oxo-1,3-dihydro-isoindol-2-yl)-piperidine-2,6-dione at a oral dose of 25 mg daily. Responses were assessed according to IWG criteria after 16 weeks of treatments. Among 15 patients receiving the treatments, 11 patients were evaluable for toxicity, nine patients were evaluable for response (>8 wks therapy), and three patients discontinued the therapy prematurely (<2 weeks) due to cholecystitis, autoimmune hemolytic anemia, or patient refusal. Median age of the patients was 78 years ranging from 51 to 82 years. FAB types of the MDS patients include RA [4 patients], RARS [4 patients], RAEB [6 patients], and RAEB-T [1 patient] with corresponding IPSS categories of Low/Int-1 in 11 patients and Int-2/High in four patients. Myelosuppression, which was characterized by higher than grade 3 common toxicity criteria or 50% decrease in leukocyte and platelet counts [9 patients], and grade 3 fatigue [1 patient], necessitated dose reduction to 10 mg in the initial ten patients. All subsequent patients initiated oral administrations with 10 mg daily. Grade 1,2 drug-related adverse effects were limited to the 25 mg dose and included pruritus or itchy scalp [6 patients] and myalgia [1 patient]. Six (66%) of nine evaluable patients experienced hematologic benefit (dual lineage, 1 patient), including 6/7 (86%) patients with IPSS Low/Int-1. Hematologic responses included RBC transfusion-independence [4 patients], decrease in RBC transfusions of more than 50% [1 patient], increase in Hgb of more than 1.5 g [1 patient], and one minor platelet response (increase of more than 30,000/μL). Among five patients evaluable for cytogenetic response, three patients achieved either a complete or partial (decrease in abnormal metaphases of more than 50%) remission. Responses were associated with normalization of blast percentage [1 patient], reduced grade of BM cytologic dysplasia, and 50% to more than 40 times improvement in BM multipotent progenitor (CFU-GEMM) and erythroid burst (BFU-E) formation. Correlation with changes in apoptotic index, angiogenic features (cellular/plasma VEGF, microvessel density), cytokine generation, and proliferative fraction (Ki67) are in progress. The results of this study indicate that 3-(4-amino-1-oxo-1,3-dihydro-isoindol-2-yl)-piperidine-2,6-dione has remarkable erythropoietic and cytogenetic remitting activity in patients with low/intermediate-1 risk MDS. Clinical benefit appears greatest in patients with low/intermediate-1 disease or the 5q-syndrome, associated with resolution of cytology dysplasia. The increase in apoptotic index, restoration of CFC, and suppression of karyotypic abnormalities suggest that the compound accelerates extinction of myelodysplastic clones. Based upon these data, the study has been expanded to treat additional subjects. Treatment with 10 mg as a continuous oral daily dose is well-tolerated with minimal myelosuppression.

Expanded Study

The clinical study was expanded with additional 16 MDS patients for at least eight weeks. According to the IPSS, 13 of these patients were categorized as low- or intermediate-1-risk patients and three patients were grouped as intermediate-2- or high-risk patients. According to the FAB classification, there were 11 patients with refractory anemia (RA) or RA with ringed sideroblasts (RARS), and five patients with RA with excess blasts (RAEB), RAEB in transformation (RAEB-T). The starting dose of 3-(4-amino-1-oxo-1,3-dihydro-isoindol-2-yl)-piperidine-2,6-dione was 25 mg daily for the first 13 patients and 10 mg daily for the remaining three patients. All patients receiving the starting dose of 25 mg required dose reduction by the completion of eight weeks therapy. Among these 16 patients who completed at least 8 weeks of monitoring, nine patients achieved an erythroid response as assessed by the International MDS Working Group Criteria. The erythroid responses consisted of transfusion independence in seven previously transfusion-dependent patients, a >2 g/dL rise in blood hemoglobin concentration in one patient in with transfusion-independent anemia, and a >50% decrease in RBC transfusion requirement in one transfusion-dependent patient. Therefore, a major erythroid response developed in eight of 16 patients and a minor erythroid response was observed in one patient. All of nine patients who showed erythroid response were low- or intermediate-1-risk patients. One patient also had a minor platelet response. In addition, complete cytogenetic responses developed in five in eight patients with abnormal karyotypes at baseline. These five patients with complete cytogenetic responses all had the Del5q31-33 abnormality, which has been discovered to be a good prognostic factor for MDS. Indeed, all five patients who enrolled in this study with 5q-syndrome achieved a complete cytogenetic response and a major erythroid response. The study also indicated an association of this therapy with an increased apoptotic index for myelodysplastic progenitors and recovery of normal hematopoietic progenitor cells.

5.4. Cycling Therapy in MDS Patients

As mentioned above, immunomodulatory compounds of the invention can be cyclically administered to patients with MDS. Cycling therapy involves the administration of a first agent for a period of time, followed by the administration of the agent and/or the second agent for a period of time and repeating this sequential administration. Cycling therapy can reduce the development of resistance to one or more of the therapies, avoid or reduce the side effects of one of the therapies, and/or improves the efficacy of the treatment.

Example 1

In a specific embodiment, prophylactic or therapeutic agents are administered in a cycle of about 16 weeks, about once or twice every day. One cycle can comprise the administration of a therapeutic on prophylactic agent and at least one (1), two (2), or three (3) weeks of rest. The number of cycles administered is from about 1 to about 12 cycles, more typically from about 2 to about 10 cycles, and more typically from about 2 to about 8 cycles.

Example 2

The objectives of the study are to evaluate the efficacy and safety of oral administration of 3-(4-amino-1-oxo-1,3-dihydro-isoindol-2-yl)-piperidine-2,6-dione in patients with MDS. Patients receive the compound in an amount of 10 mg/d or 15 mg/d for 21 days every 28 days in 4-week cycles for 16 weeks (4 cycles) or 24 weeks (6 cycles). The subject population comprises patients with low- or intermediate-1-risk MDS (International Prognostic Scoring System) with red blood cell transfusion-dependent anemia who have received at least two units of RBCs within 8 week of baseline (first day of study treatment). In addition to hematological laboratory monitoring, bone marrow aspirates/biopsies with cytogenic analyses are obtained at baseline, after the completion of 3 cycles and after the completion of 6 cycles. The bone marrow, safety and efficacy data are reviewed to assess benefit-to-risk considerations throughout the study. The study reviews red blood cell transfusion independence and major erythroid response according to the International MDS Working Group Criteria. Further, the study observes red blood cell transfusion independence in the subgroup of patients with the 5q deletion cytogenetic abnormality; platelet, neutrophil, bone marrow and cytogenetic responses; and minor erythroid response of ≧50% but <100% reduction in red blood cell transfusion requirement over an 8 week period. The study further monitors adverse events, hematological tests, serum chemistries, TSH, urinalysis, urine or serum pregnancy tests, vital signs, ECG and physical examinations.

Example 3

The objectives of the study are to compare the efficacy and safety of oral administration of 3-(4-amino-1-oxo-1,3-dihydro-isoindol-2-yl)-piperidine-2,6-dione to that of placebo plus standard care in patients with MDS. Patients receive the therapy in 4-week cycles for 16 weeks (4 cycles) or 24 weeks (6 cycles). The subject population comprise patients with low- or intermediate-1-risk MDS (International Prognostic Scoring System) with red blood cell transfusion-dependent anemia who have received at least two units of RBCs within 8 week of baseline (first day of study treatment). The study visits to assess safety and efficacy occur every 4 weeks and hematologic laboratory monitoring is performed every 2 weeks. Bone marrow aspirates/biopsies with cytogenetic analyses are obtained at baseline after the completion of 3 cycles and after the completion of 6 cycles. Bone marrow findings, safety and efficacy data are reviewed to assess benefit-to-risk considerations throughout the study. An extension study of continued treatments with the administration of the compound is available for patients who derive clinical benefit from 6 cycles of the therapy and to provide an opportunity for subjects who were randomized to placebo to cross over to the therapy.

Embodiments of the invention described herein are only a sampling of the scope of the invention. The full scope of the invention is better understood with reference to the attached claims.

What is claimed is:

1. A method of treating a myelodysplastic syndrome, which comprises (a) administering to a patient in need thereof about 0.1 mg per day to about 10 mg per day of 4-(amino)-2-(2,6-dioxo(3-piperidyl))-isoindoline-1,3-dione of formula:

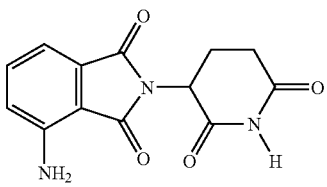

or a pharmaceutically acceptable salt, solvate or stereoisomer thereof for a period of time followed by a period of rest; and (b) repeating step (a).

2. The method of claim 1, wherein the compound is a pharmaceutically acceptable salt.

3. The method of claim 1, wherein the compound is a pharmaceutically acceptable solvate.

4. The method of claim 1, wherein the stereoisomer is an enantiomerically pure R isomer or S isomer.

5. The method of claim 1, which further comprises
   (c) administering a therapeutically effective amount of a second active agent for a period of time followed by a period of rest; and
   (d) repeating step (c).

6. The method of claim 5, wherein the second active agent is capable of improving blood cell production.

7. The method of claim 5, wherein the second active agent is a cytokine, hematopoietic growth factor, an anti-cancer agent, an antibiotic, a proteasome inhibitor, or an immunosuppressive agent.

8. The method of claim 5, wherein the second active agent is etanercept, imatinib, anti-TNF-α antibodies, infliximab, G-CSF, GM-CSF, EPO, topotecan, pentoxifylline, ciprofloxacin, irinotecan, vinblastine, dexamethasone, IL2, IL8, IL18, Ara-C, vinorelbine, isotretinoin, 13-cis-retinoic acid, arsenic trioxide, or a pharmacologically active mutant or derivative thereof.

9. The method of claim 1, wherein the myelodysplastic syndrome is refractory anemia, refractory anemia with ringed sideroblasts, refractory anemia with excess blasts, refractory anemia with excess blasts in transformation, or chronic myelomonocytic leukemia.

10. The method of claim 1, wherein the compound is administered orally.

11. The method of claim 10, wherein the compound is administered in the form of a capsule or tablet.

12. The method of claim 1, wherein the number of cycle is from one to twelve cycles.

13. The method of claim 1, the compound is administered in an amount of from about 0.1 to about 10 mg per day for 21 days every 28 days for sixteen or twenty-four weeks.

14. The method of claim 1, wherein the compound is administered in an amount of from about 0.1 mg per day to about 10 mg per day for 21 days followed by seven days of rest in a 28 days cycle.

15. The method of claim 1, wherein the compound is administered orally in an amount of 0.1 mg, 1 mg, 2 mg, 2.5 mg, 5 mg or 10 mg as a capsule per day.

16. The method of claim 1, wherein the 4-(amino)-2-(2,6-dioxo(3-piperidyl))-isoindoline-1,3-dione is administered.

17. The method of claim 5, wherein the second active agent is azacytidine.

* * * * *